United States Patent
Baynham

(10) Patent No.: US 9,974,574 B2
(45) Date of Patent: May 22, 2018

(54) ANTERIOR CERVICAL DISC REPLACEMENT

(71) Applicant: Atlas Spine, Inc., Jupiter, FL (US)

(72) Inventor: Matthew G. Baynham, Jupiter, FL (US)

(73) Assignee: Atlas Spine, Inc., Jupiter, FL (US)

( * ) Notice: Subject to any disclaimer, the term of this patent is extended or adjusted under 35 U.S.C. 154(b) by 494 days.

(21) Appl. No.: 14/657,583

(22) Filed: Mar. 13, 2015

(65) Prior Publication Data
US 2015/0257796 A1  Sep. 17, 2015

Related U.S. Application Data

(60) Provisional application No. 61/953,631, filed on Mar. 14, 2014.

(51) Int. Cl.
*A61B 17/70* (2006.01)
*A61B 17/00* (2006.01)
*A61F 2/30* (2006.01)

(52) U.S. Cl.
CPC ...... *A61B 17/7059* (2013.01); *A61B 2017/00004* (2013.01); *A61B 2017/00955* (2013.01); *A61F 2002/3006* (2013.01)

(58) Field of Classification Search
CPC .................................................. A61B 17/7059
See application file for complete search history.

(56) References Cited

U.S. PATENT DOCUMENTS

| | | | |
|---|---|---|---|
| 6,419,704 B1 * | 7/2002 | Ferree | A61F 2/441 623/17.12 |
| 8,470,039 B2 * | 6/2013 | Blain | A61B 17/7059 623/17.11 |

\* cited by examiner

*Primary Examiner* — Kevin Truong
*Assistant Examiner* — Olivia C Chang
(74) *Attorney, Agent, or Firm* — McHale & Slavin, P.A.

(57) ABSTRACT

Disclosed is a cervical plate having a polyester staple fiber laminated within a polycarbonate urethane. The polyurethane provides a flexible, high resilience structure with a Dacron® material providing a flexible skeleton. The result is a cervical plate that is flexible but provides the necessary rigidity. An inflatable balloon can be used to mimic the properties of the natural disc by maintaining the intervertebral disc space through a full range of natural motion.

4 Claims, 5 Drawing Sheets

ANTERIOR CERVICAL DISC REPLACEMENT

PRIORITY CLAIM

In accordance with 37 C.F.R. 1.76, a claim of priority is included in an Application Data Sheet filed concurrently herewith. Accordingly, the present invention claims priority to U.S. Provisional Patent Application No. 61/953,631, entitled "ANTERIOR CERVICAL DISC REPLACEMENT", filed Mar. 14, 2014. The contents of the above referenced application is incorporated herein by reference in its entirety.

FIELD OF THE INVENTION

The present invention relates generally to surgically-implantable spinal devices and, more specifically, to an anterior cervical disc replacement.

BACKGROUND OF THE INVENTION

Anterior cervical plates can be used for fixation of the cervical spine. The structure of the intervertebral disc disposed between the cervical bones comprises a peripheral fibrous shroud (the annulus) which circumscribes a spheroid of flexibly deformable material (the nucleus). The nucleus comprises a hydrophilic, elastomeric cartilaginous substance that cushions and supports the separation between the bones while also permitting articulation of the two vertebral bones relative to one another to the extent such articulation is allowed by the other soft tissue and bony structures surrounding the disc.

Traumatic, genetic, and long term wearing phenomena contribute to the degeneration of the nucleus. This degeneration of this critical disc material, from the hydrated, elastomeric material that supports the separation and flexibility of the vertebral bones, to a flattened and inflexible state, affects the mobility of the segment, and can cause significant pain. In many instances the vertebral bones are best if simply immobilized which is performed by securing two or more discs together.

Immobilization is achieved by attaching metal plates to the anterior or posterior elements of the cervical spine, and the insertion of some osteoconductive material (autograft, allograft, or other porous material) between the adjacent vertebrae of the segment. This sacrifice of mobility at the immobilized, or fused, segment, can affect the patient's surrounding joint segments.

The screws used to attach the plates required locking mechanisms to prevent premature loosening due to the rigidity of the plate. Numerous prior art references address such locking screws, however, the prior art fails to address the construction of the plate.

The use of an expandable balloon like artificial disc prosthesis filled with a polymer is known. A joint arthroplasty device can be formed in situ by inserting a hollow device having an aperture and a lumen into a target joint, and injecting material into the hollow device to form an implant. An artificial/prosthetic facet joint with balloon joint space component composed of latex, polymer, silicone or the like materials.

What is needed in the art is an anterior cervical disc that is formed from a polycarbonate having a fabric skeleton structure that can include an inflatable balloon to mimic the properties of the natural disc by maintaining the intervertebral disc space through a full range of natural motion and absorb the shocks of daily use.

SUMMARY OF THE INVENTION

Disclosed is a cervical plate having a hydrotec fiber, such as Dacron® polyester staple fiber, laminated within polycarbonate joined by carbamate (urethane) links. The polyurethane provides a flexible, high resilience structure with the Dacron® material providing a flexible skeleton. The result is a cervical plate that is flexible but provides the necessary rigidity. Should the patient receive an impact, such as jumping, the cervical plate has limited flexibility allowing the plate to absorb the shock, lessening the loading on the mounting screws. In addition, an inflatable balloon can be used to mimic the properties of the natural disc by maintaining the intervertebral disc space through a full range of natural motion.

Other objectives and advantages of this invention will become apparent from the following description taken in conjunction with any accompanying drawings wherein are set forth, by way of illustration and example, certain embodiments of this invention. Any drawings contained herein constitute a part of this specification and include exemplary embodiments of the present invention and illustrate various objects and features thereof.

DETAILED DESCRIPTION OF THE INVENTION

Figure 1:
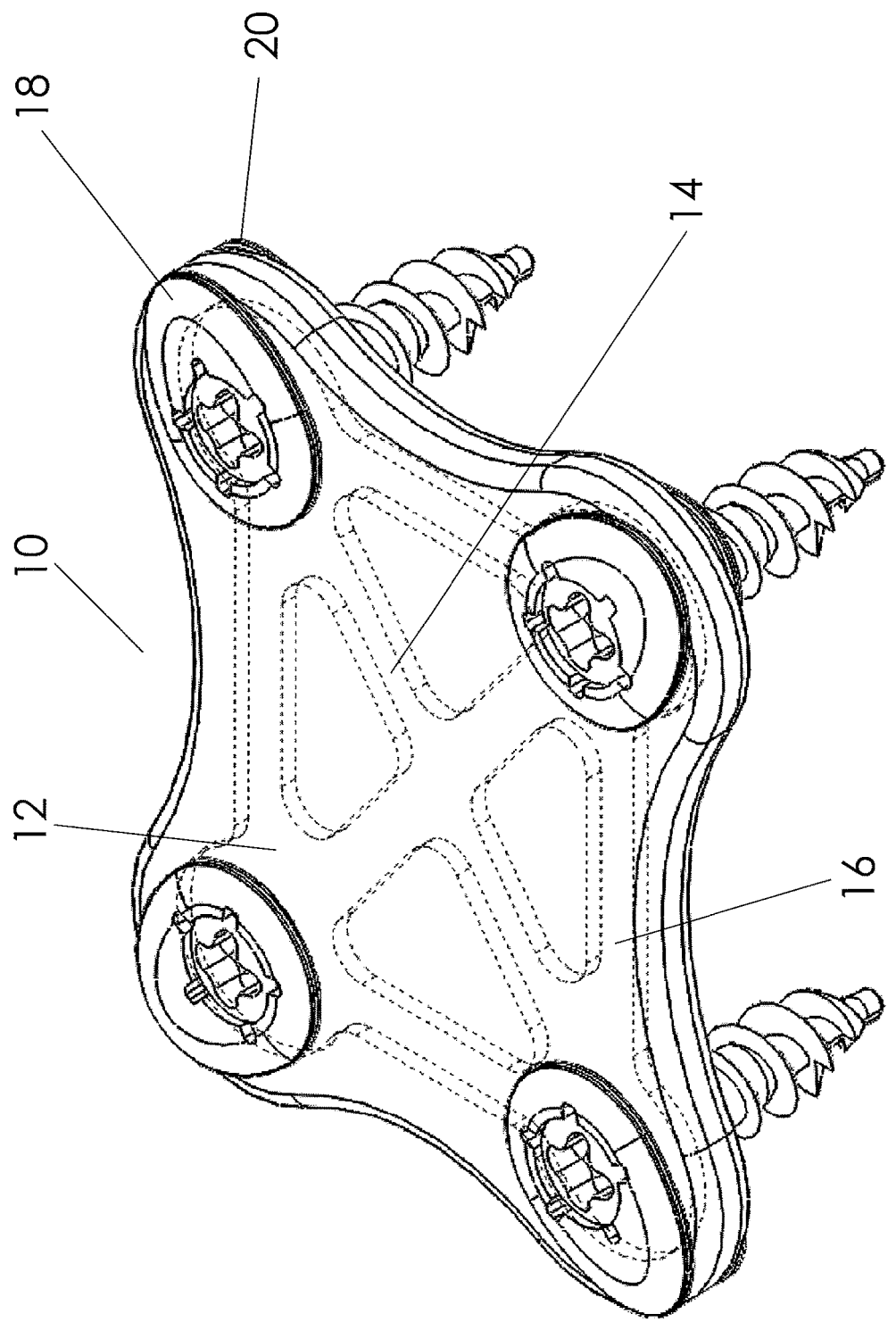
FIG. 1 is a perspective view of the cervical disc of the instant invention.

FIG. 1 depicts the plate 10 of the instant invention having a skeleton structure 12 formed from a Dacron® polyester staple fiber constructed and arranged with a cross section 14 with border sections 16 have screw hole apertures that form around each of the mounting screws 18. The skeleton structure 12 is laminated within a polycarbonate base 20 having urethane links. The polyurethane provides a flexible, high resilience structure with the Dacron® material providing a flexible skeleton.

Figure 2:
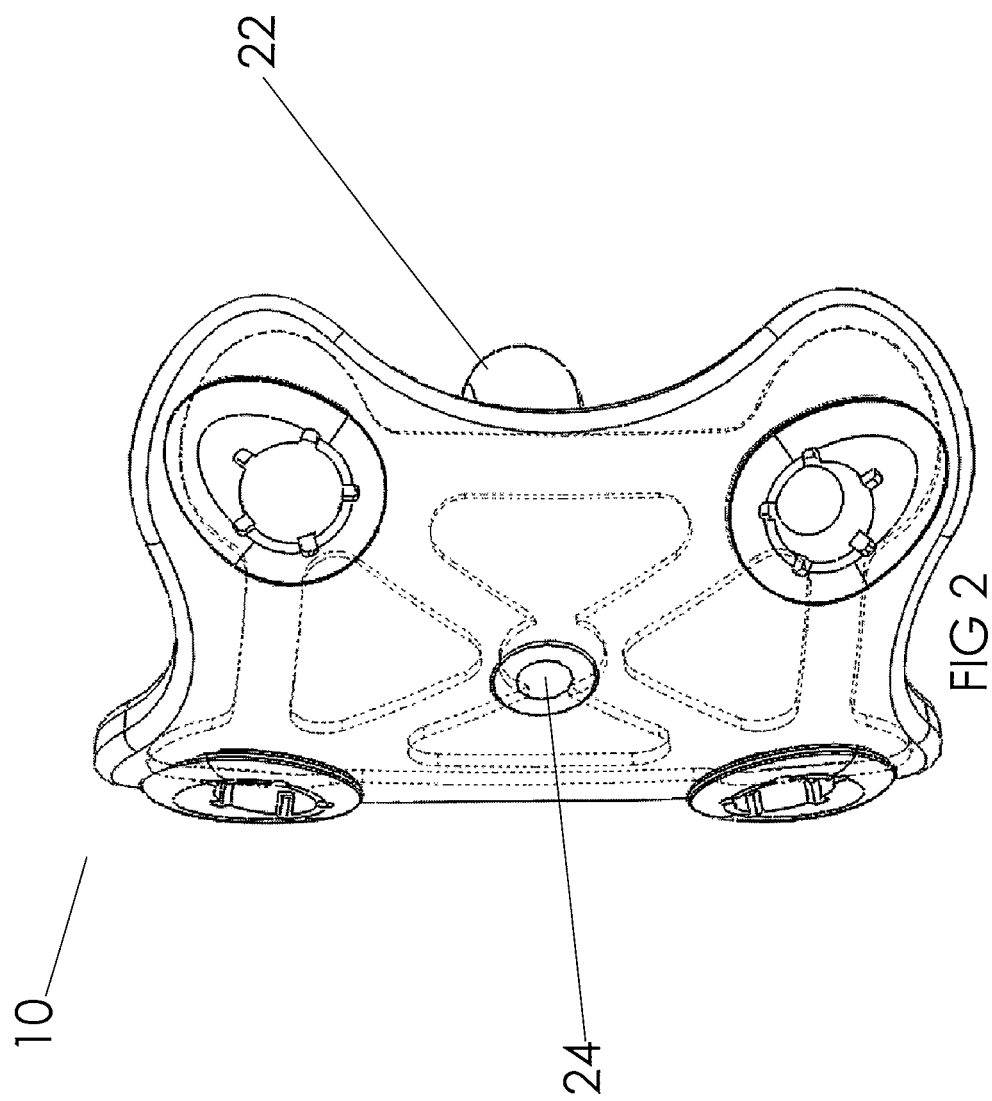
FIG. 2 is a front perspective alternative embodiment of the cervical plate that includes an inflatable balloon.
Figure 3:
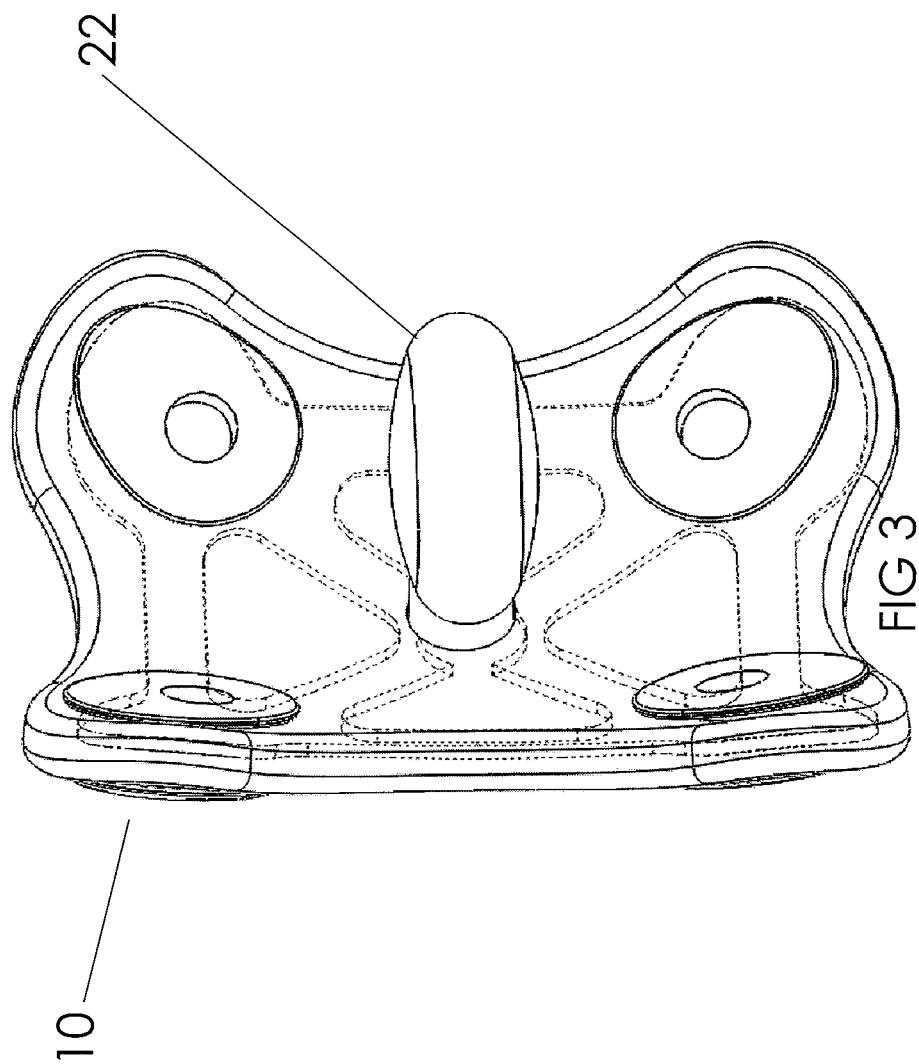
FIG. 3 is a rear perspective view thereof.
Figure 4:
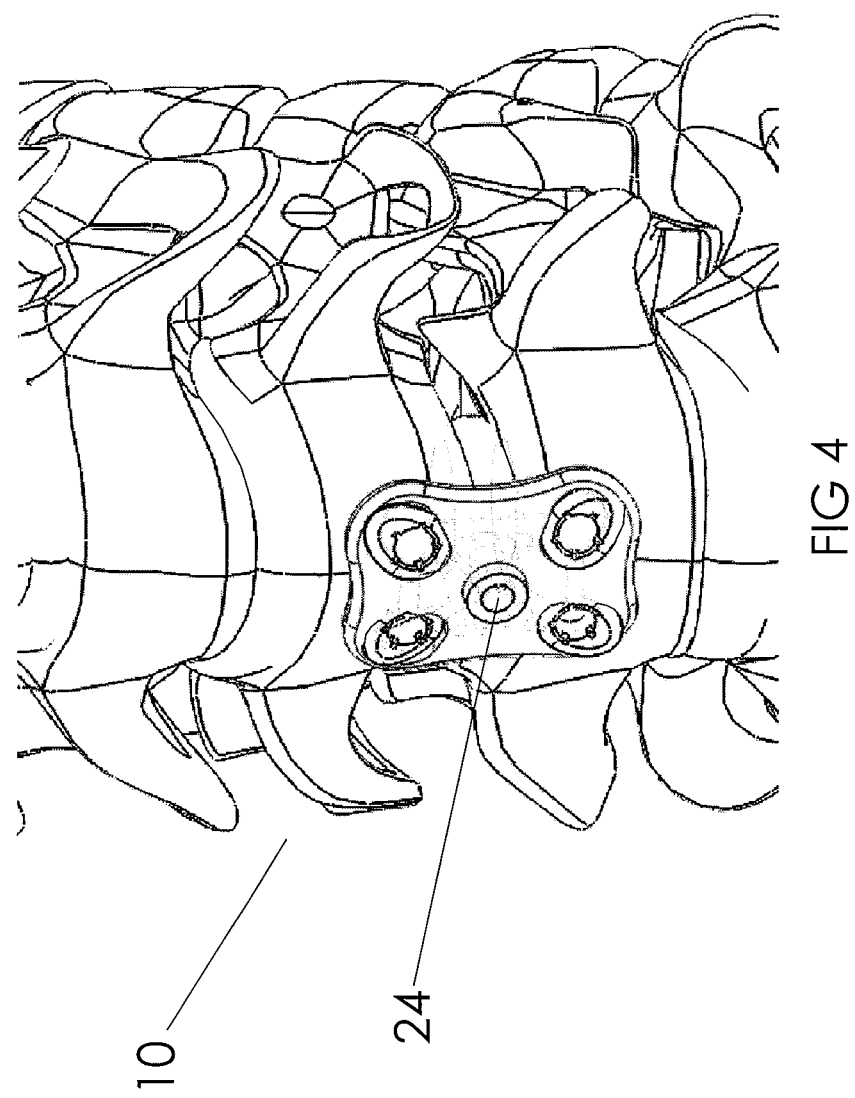
FIG. 4 is pictorial view of a spine with cervical plate installed.
Figure 5:
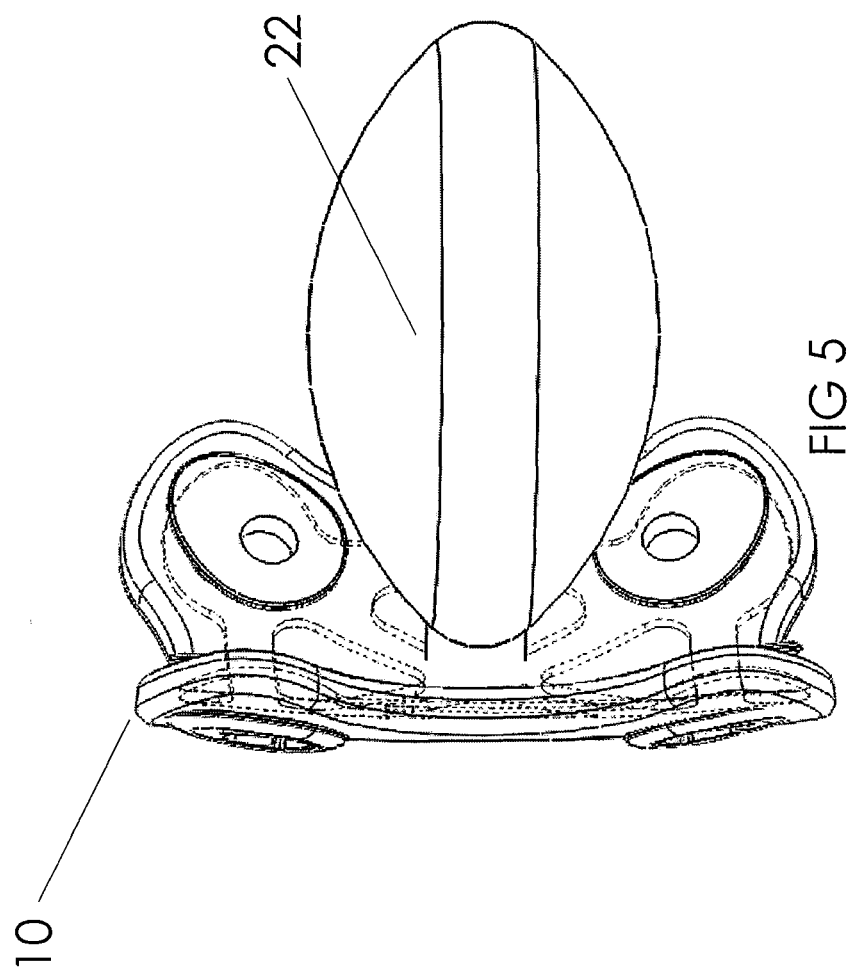
FIG. 5 is a pictorial view of the cervical plate.

FIGS. 2-4 depicts a balloon 22 that can be filled with a fluid through a one way valve 24 to secure the fluid within the balloon. Suitable volumetric materials can be viscous and non-viscous including saline, gels, latex, polymers, polyethylenes, silicones, polyurethanes, metallics, ceramics, collagen, or hydrogels. Volumetric materials can be radio-opaque contrast agents, allowing fluoroscopic viewing during injection into the disc to a known pressure.

It is to be understood that while a certain form of the invention is illustrated, it is not to be limited to the specific form or arrangement herein described and shown. It will be apparent to those skilled in the art that various changes may be made without departing from the scope of the invention and the invention is not to be considered limited to what is shown and described in the specification and any drawings/figures included herein.

One skilled in the art will readily appreciate that the present invention is well adapted to carry out the objectives and obtain the ends and advantages mentioned, as well as those inherent therein. The embodiments, methods, procedures and techniques described herein are presently representative of the preferred embodiments, are intended to be exemplary and are not intended as limitations on the scope. Changes therein and other uses will occur to those skilled in the art which are encompassed within the spirit of the invention and are defined by the scope of the appended claims. Although the invention has been described in connection with specific preferred embodiments, it should be understood that the invention as claimed should not be unduly limited to such specific embodiments. Indeed, various modifications of the described modes for carrying out the invention which are obvious to those skilled in the art are intended to be within the scope of the following claims.

What is claimed is:

1. A flexible cervical plate comprising: a structure formed from four polyester staple fiber border sections each adjoined at a corner to define a substantially rectangular shape with a screw hold aperture positioned at each said corner, said structure including a polyester staple fiber cross member linking each corner with a diagonally positioned corner;
   a polycarbonate coating said polyester staple fiber border sections and said cross member;
   a balloon secured centrally disposed on a lower surface of said cross member of said structure;
   a one way valve secured to an upper surface of said cross member, said valve fluidly coupled to said balloon for receipt of a volumetric material;
   wherein said cervical plate is held in position by mounting screws placed through said screw hold apertures with said balloon configured to extend into an intervertebral disc space.

2. The flexible cervical plate according to claim 1 wherein said volumetric material is selected from the group consisting of: saline, gels, latex, polymers, polyethylenes, silicones, polyurethanes, metallics, ceramics, collagen, or hydrogels.

3. The flexible cervical plate according to claim 1 wherein said volumetric material is viscous.

4. The flexible cervical plate according to claim 1 wherein said volumetric material is non-viscous.

* * * * *